United States Patent
Kang et al.

(10) Patent No.: US 9,000,400 B2
(45) Date of Patent: Apr. 7, 2015

(54) PORTABLE ULTRAVIOLET DEVICE FOR EXPLORING MINERAL RESOURCE

(75) Inventors: Il-Mo Kang, Seoul (KR); Ki-Min Roh, Seoul (KR); Se-Jung Chi, Seoul (KR); Sang-Mo Koh, Daejeon (KR); Chul-Ho Heo, Seoul (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 247 days.

(21) Appl. No.: 13/481,625

(22) Filed: May 25, 2012

(65) Prior Publication Data

US 2013/0240755 A1  Sep. 19, 2013

(30) Foreign Application Priority Data

Mar. 19, 2012 (KR) .................. 10-2012-0027719

(51) Int. Cl.
*G01N 21/64* (2006.01)
*A61B 5/00* (2006.01)

(52) U.S. Cl.
CPC ............ *A61B 5/0071* (2013.01); *A61B 2562/16* (2013.01); *G01N 21/6447* (2013.01); *G01N 21/64* (2013.01)

(58) Field of Classification Search
CPC ............. A61B 5/0071; A61B 2562/00; A61B 2562/16; A61B 2562/221; G01N 21/64; G01N 21/21; G01N 21/474; G01N 21/4686; G01N 21/6447; G01N 21/87; G01N 21/88; G01N 33/24; G01V 8/02; G01V 8/00; F21V 21/00; F21V 21/30; F21V 21/26; F21V 21/28; F21V 21/29; F21V 14/02; F21V 14/025; F21V 14/00; F21S 48/1726
USPC ......... 362/257, 269, 260, 277, 280–289, 317, 362/319, 322, 372; 250/234, 458.1, 459.1, 250/432 R, 428, 578.1

See application file for complete search history.

(56) References Cited

U.S. PATENT DOCUMENTS

| | | | | |
|---|---|---|---|---|
| 2,874,302 | A * | 2/1959 | Mallory et al. ............ | 250/485.1 |
| 5,019,849 | A * | 5/1991 | Harrison .................... | 396/592 |
| 5,412,219 | A * | 5/1995 | Chappelle et al. ......... | 250/461.1 |
| 2003/0161142 | A1* | 8/2003 | Kotovsky .................... | 362/147 |
| 2008/0224069 | A1* | 9/2008 | Feyher ....................... | 250/461.1 |
| 2009/0284975 | A1* | 11/2009 | Querci ........................ | 362/285 |

FOREIGN PATENT DOCUMENTS

| | | |
|---|---|---|
| JP | 1997-318543 | 12/1997 |
| JP | 1999-064222 | 3/1999 |

* cited by examiner

*Primary Examiner* — Yara B Green
(74) *Attorney, Agent, or Firm* — Kile Park Reed & Houtteman PLLC

(57) ABSTRACT

Provided is a portable ultraviolet device for exploring a mineral resource. The portable ultraviolet device for exploring the mineral resource may include a body, a visible component, an ultraviolet lamp assembly, and a darkroom component. The visible component is coupled to the body to pass through the body so that a mineral resource disposed at a lower portion of the body is observed from an upper side of the body. The ultraviolet lamp assembly part is coupled to the body to emit ultraviolet rays onto the mineral resource. The darkroom component is coupled to a bottom surface of the body to surround the visible component and the ultraviolet lamp assembly and defines an external light blocking space having an openable inlet in a lower portion of the body.

12 Claims, 6 Drawing Sheets

PORTABLE ULTRAVIOLET DEVICE FOR EXPLORING MINERAL RESOURCE

CROSS-REFERENCE TO RELATED APPLICATION

This application claims priority to Korean Patent Application No. 10-2012-0027719 filed on Mar. 19, 2012 and all the benefits accruing therefrom under 35 U.S.C. §119, the contents of which are incorporated by reference in their entirety.

BACKGROUND

The present disclosure relates to a portable ultraviolet device for exploring a mineral resource, and more particularly, to a portable ultraviolet device for exploring a mineral resource which distinguishes a fluorescent material emitting proper visible light when an ultraviolet ray is emitted onto the fluorescent material.

When an ultraviolet (UV) ray having a specific wavelength is emitted onto a mineral that is called a fluorescent mineral, the fluorescent mineral emits a visible light having a specific color. The fluorescent mineral often contains useful elements in industrial fields. For example, in case of scheelite, when an UV ray having a short wavelength of about 254 nm is emitted onto the scheelite, the scheelite emits light a bluey-whiteness color. Here, the scheelite contains 63.85 weight % of tungsten (W). For another example, in case of powellite, when the UV ray having the short wavelength of about 254 nm is emitted onto the powellite, the powellite emits light having a yellow color. Here, the powellite contains 47.97 weight % of molybdenum (Mo). Thus, when the ultraviolet device for exploring a mineral resource is used, fluorescent minerals containing useful elements may be facilely distinguished.

However, to confirm visible light emitted during the fluorescence, an inflow of light from its surroundings should be intercepted. Thus, a conventional UV device for exploring a mineral resource may be limited in use and only used at night or within a tunnel in which external light is intercepted. Considering that exploration is mainly performed during the daytime, a need exists to develop a device which can confirm fluorescent minerals even during the daytime, thereby increasing efficiency of outdoor mineral exploration.

SUMMARY

The present disclosure provides a portable UV device for exploring a mineral resource which can explore a fluorescent mineral in the open air during the daytime.

In accordance with an exemplary embodiment, a portable ultraviolet (UV) device for exploring the mineral resource includes a body, a visible component, an ultraviolet lamp assembly, and a darkroom. The visible component is coupled to the body to pass through the body so that the mineral resource disposed at a lower portion of the body is observed from an upper side of the body. The UV lamp assembly is coupled to the body to emit UV rays onto the mineral resource. The darkroom component is coupled to a bottom surface of the body to surround the visible part and the UV lamp assembly and defines an external light blocking space having an openable inlet in a lower portion of the body.

The body may have a first sealed inner space through which the visible part passes and two second inner spaces opened downward and spaced from each other with the first inner space there between. The UV lamp assembly may include a first UV lamp inserted into one of the two second inner spaces and is coupled to the body. A second UV lamp is inserted into the other one of the two second inner spaces and is coupled to the body. The first UV lamp assembly includes a first UV lamp extending in a first direction, a downwardly opened first receiving container coupled to the body to receive the first UV lamp, and a first UV filter coupled to an opening of the first receiving container. The second UV lamp assembly includes a second UV lamp generally extending in the first direction, a downwardly opened second receiving container coupled to the body to receive the second UV lamp, and a second UV filter coupled to an opening of the second receiving container.

The portable UV device may further include a first power supply a first printed circuit board, a second power supply, and a second printed circuit board. The first power supply may be received in the first inner space to generate a first power, and the first printed circuit board may be received in the first inner space to transmit the first power to the first UV lamp. The second power supply part may be received in the first inner space to generate a second power, and the second printed circuit board may be received in the first inner space to transmit the second power to the second UV lamp.

The first and second receiving containers may be rotatably coupled to the body about a first rotation axis parallel to the first direction. Each of the first and second receiving containers may include first and second coupling projections respectively protruding from both ends with respect to the first direction, and the bottom surface of the body may include first and second coupling rings having coupling grooves in which the first and second coupling projections of the first receiving container are respectively inserted and third and fourth coupling rings having coupling grooves in which the first and second coupling projections of the second receiving container are respectively inserted. Each of the first and second receiving containers may include third and fourth coupling projections respectively protruding from both ends with respect to the first direction, and a sidewall of the body defining the second inner spaces may have first and second coupling holes in which third and fourth coupling projections of the first receiving container are respectively inserted and third and fourth coupling holes in which third and fourth coupling projections of the second receiving container are respectively inserted. In this case, the portable UV device may further includes: a first rotation member disposed outside the body, the first rotation member being coupled to one of the first and second coupling projections of the first receiving container to rotate the first receiving container about a rotation axis parallel to the first direction; and a second rotation member disposed outside the body, the second rotation member being coupled to one of the first and second coupling projections of the second receiving container to rotate the second receiving container about the rotation shaft parallel to the first direction. On the other hand, first and second rotation slits extending in a second direction perpendicular to the first direction and spaced from each other may be defined in a top surface of the body. The first receiving container may include a first rotation member protruding upward, inserted into the first rotation slit, and rotated in the second direction to rotate the first receiving container about the rotation axis parallel to the first direction. The second receiving container may include a second rotation member protruding upward, inserted into the second rotation slit, and rotated in the second direction to rotate the second receiving container about the rotation axis parallel to the first direction.

The darkroom component may include a plurality of supports, a light blocking layer, and an opening/closing part. The plurality of supports may be arranged to surround the visible part and the UV lamp assembly and coupled to the bottom surface of the body to protrude from the bottom surface of the body. The light blocking layer may be coupled to the plurality of supports to define the external light blocking space. The opening/closing part may be coupled to the light blocking layer to open or close an inlet of the external light blocking space. Each of the plurality of supports may be rotatably coupled to the bottom surface of the body.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
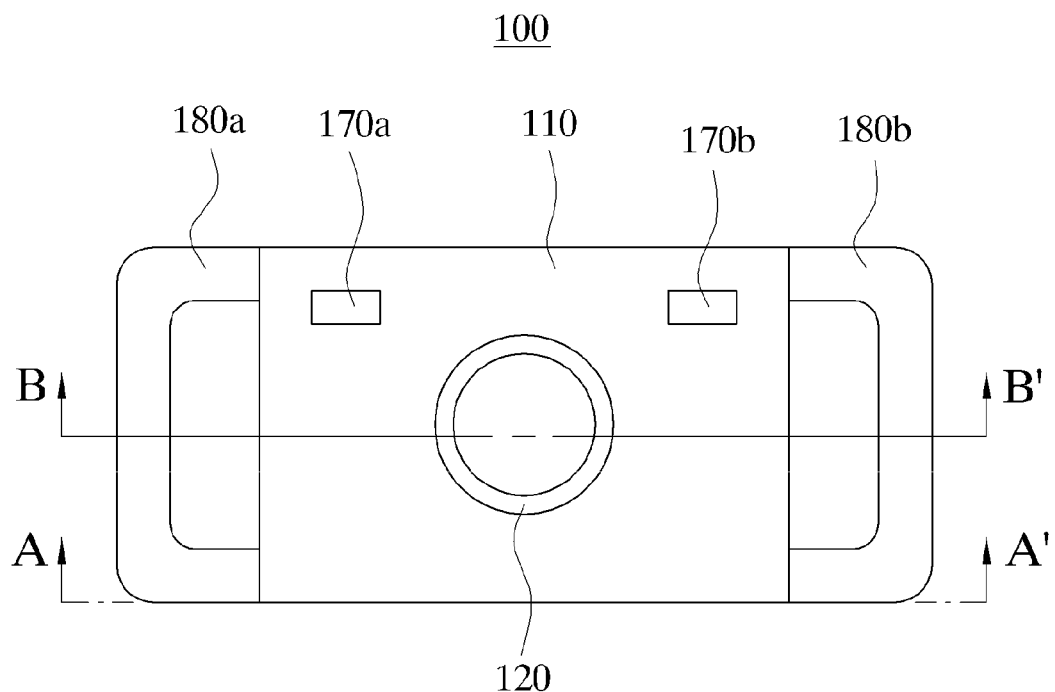
FIG. 1 is a top view of a portable ultraviolet (UV) device for exploring a mineral source in accordance with an exemplary embodiment.

Exemplary embodiments will be described in detail with reference to the accompanying drawings. Since the present disclosure may have modified embodiments, preferred embodiments are illustrated in the drawings and are described in the detailed description of the invention. However, this does not limit the present disclosure within specific embodiments and it should be understood that the present disclosure covers all the modifications, equivalents, and replacements within the idea and technical scope of the present disclosure. In the drawings, the dimensions and size of each structure are exaggerated, omitted, or schematically illustrated for convenience in description and clarity.

It will be understood that although the terms of first and second are used herein to describe various elements, these elements should not be limited by these terms. Terms are only used to distinguish one component from other components. Therefore, a component referred to as a first component in one embodiment can be referred to as a second component in another embodiment.

In the following description, the technical terms are used only for explaining a specific exemplary embodiment while not limiting the present disclosure. The terms of a singular form may include plural forms unless referred to the contrary. The meaning of 'include' or 'comprise' specifies a property, a step, a function, an element or a combination thereof, but does not exclude other properties, steps, functions, elements or combinations thereof.

Unless terms used in the present description are defined differently, the terms should be construed as having meaning known to those skilled in the art. Terms that are generally used and have been defined in dictionaries should be construed as having meanings matched with contextual meanings in the art. In this description, unless defined clearly, terms are not ideally or, excessively construed as formal meanings.

Figure 2:
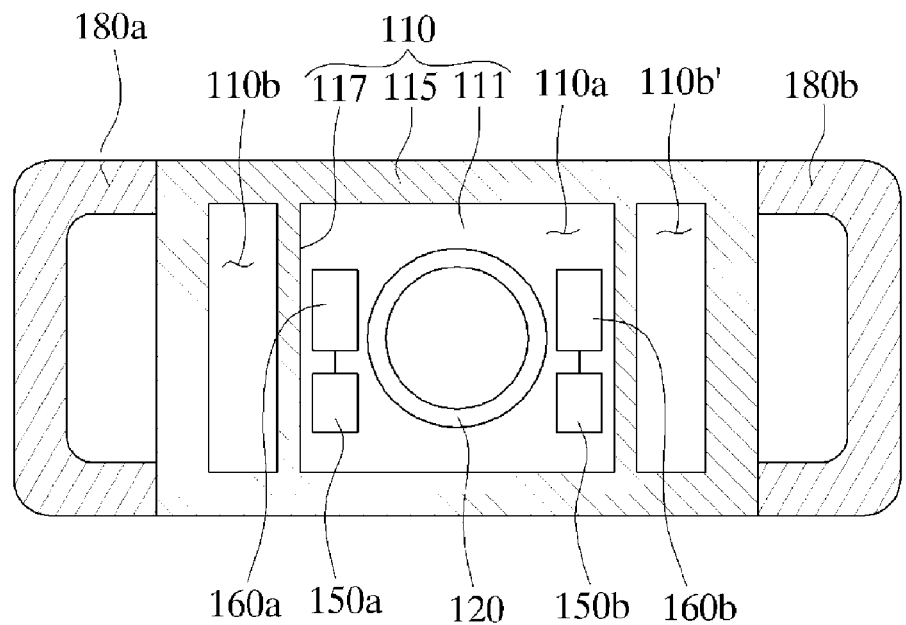
FIG. 2 is a sectional view of the portable UV device for exploring a mineral source, taken along section line A-A in a direction parallel to that of the top view of FIG. 1.
Figure 3:
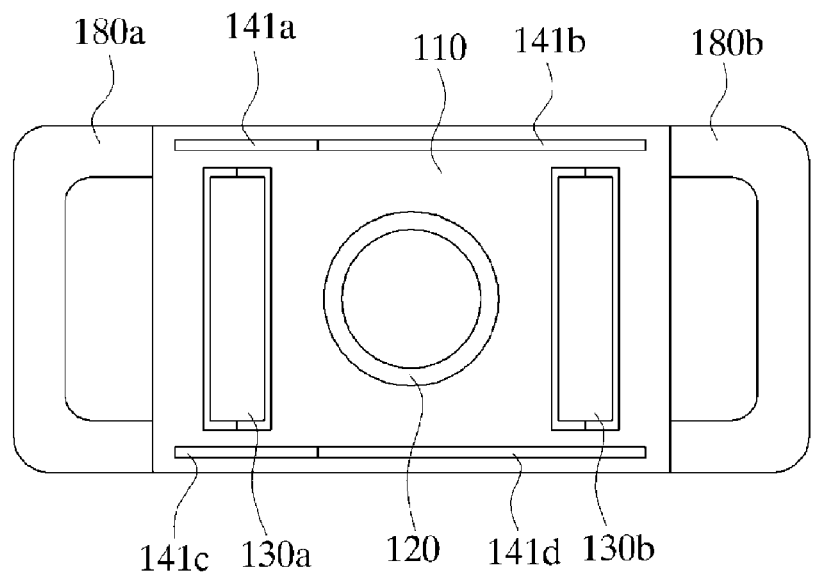
FIG. 3 is a bottom view of the portable UV device for exploring a mineral source shown in FIG. 1.
Figure 4:
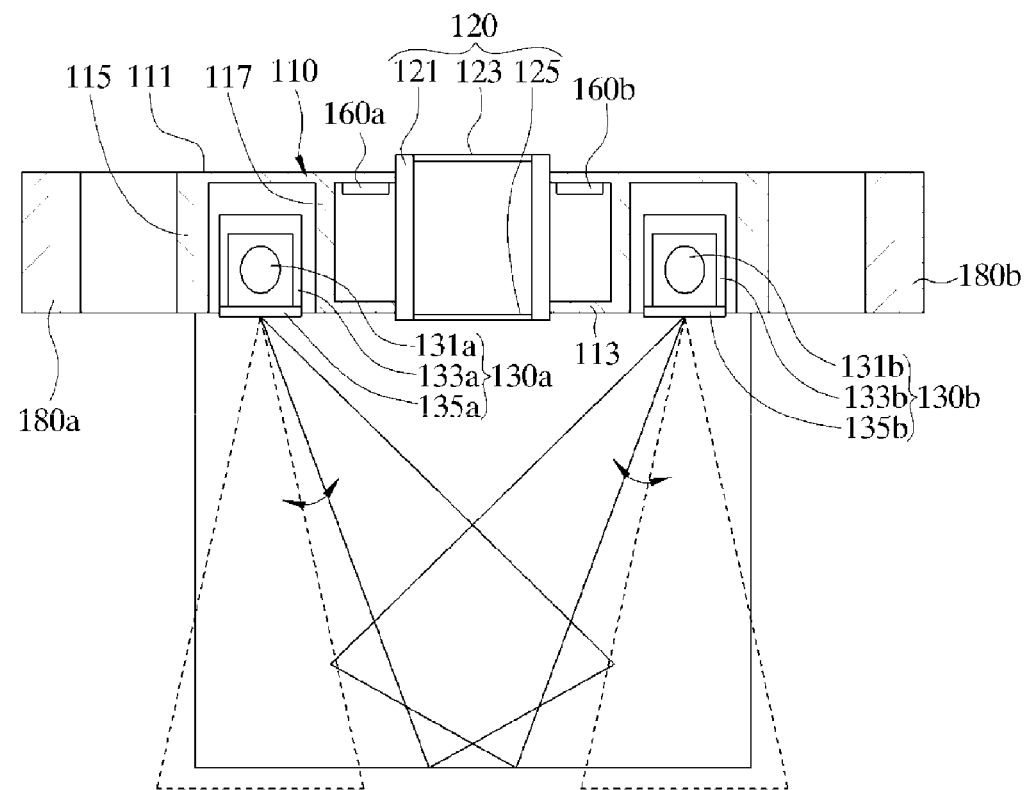
FIG. 4 is a cross sectional view taken along line B-B of FIG. 1.
Figure 5A:
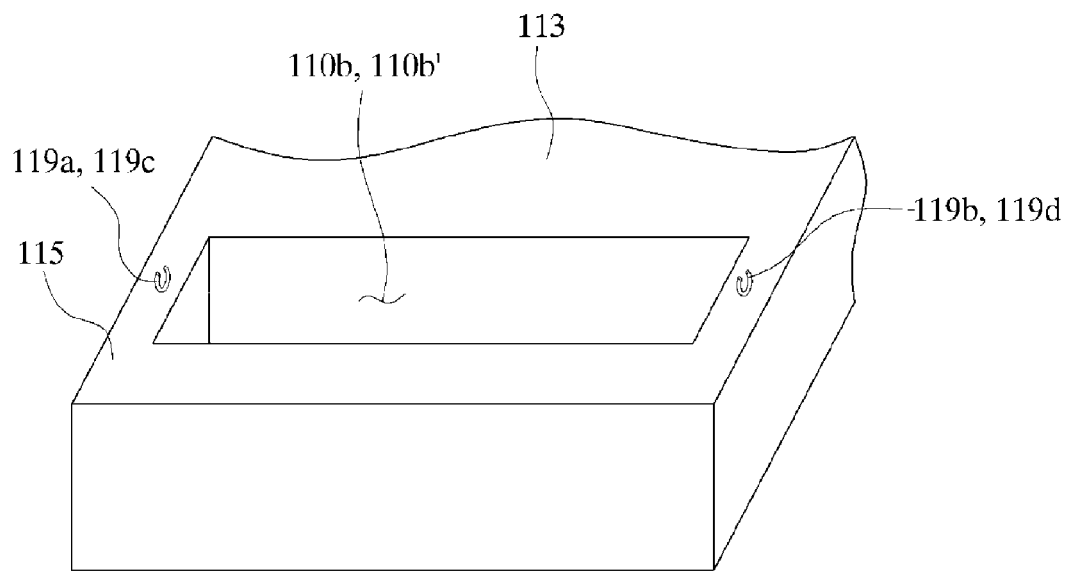
FIGS. 5A and 5B are perspective views illustrating a coupled relation between a body and a receiving container of an UV lamp assembly in accordance with an exemplary embodiment.
Figure 5B:
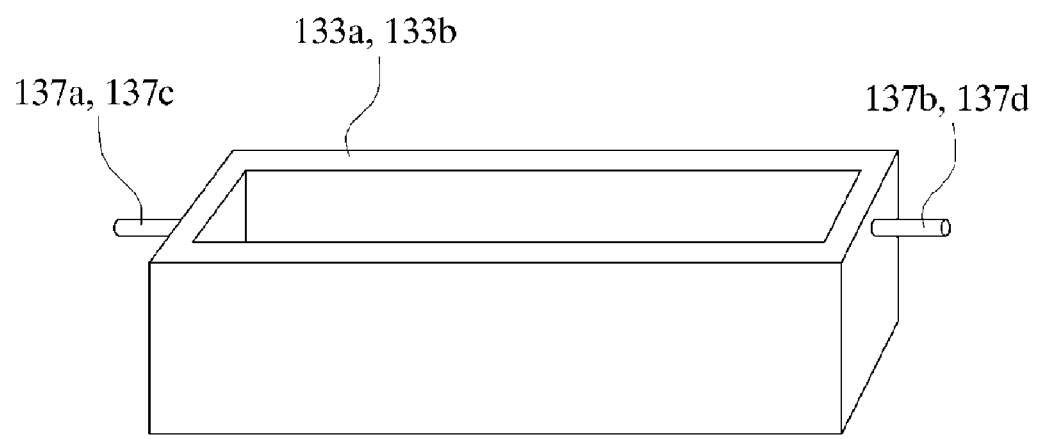
Figure 6A:
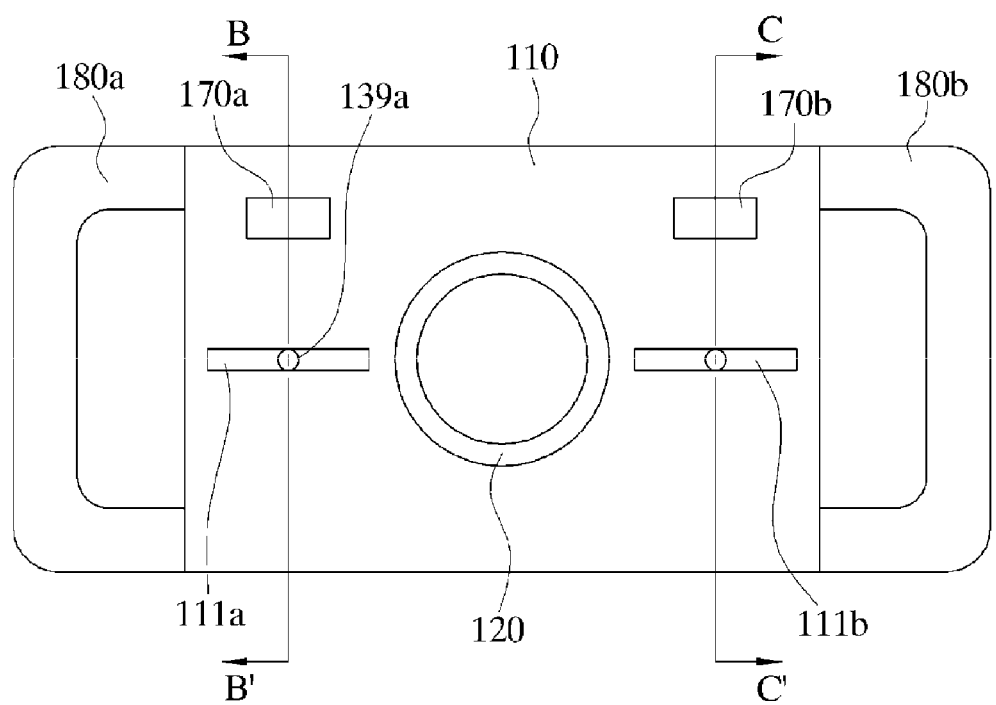
FIGS. 6A and 6B are views illustrating a coupled relation between a body and a receiving container of an UV lamp assembly in accordance with another exemplary embodiment.
Figure 6B:
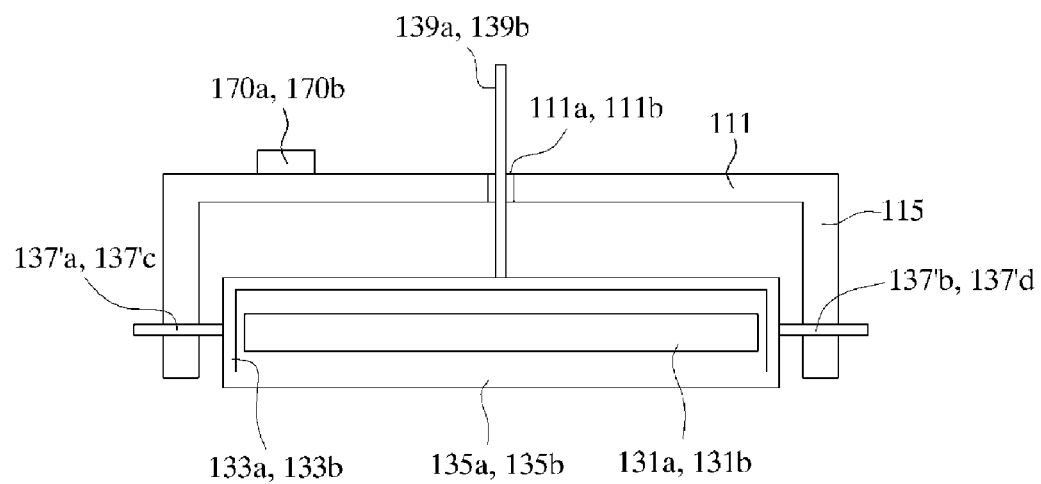
Figure 7:
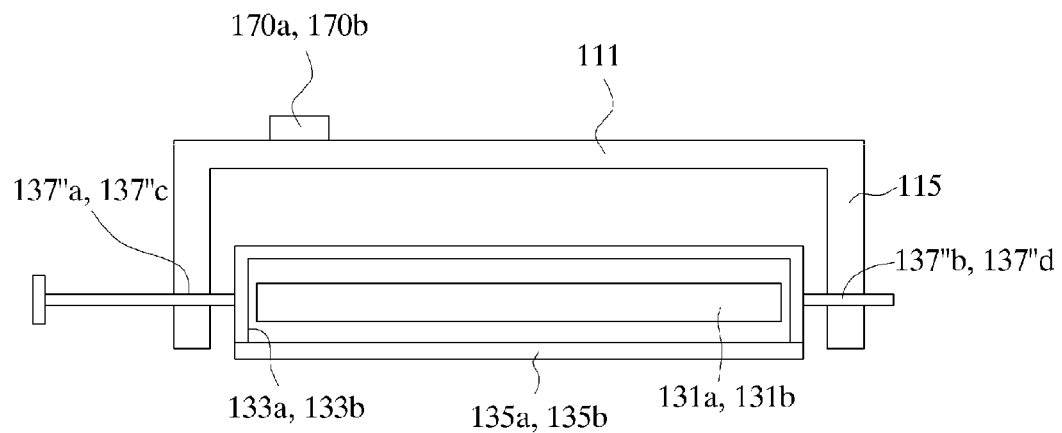
FIG. 7 is a sectional view illustrating a coupled relation between a body and a receiving container of an UV lamp assembly in accordance with another exemplary embodiment.

FIG. 1 is a top view of a portable ultraviolet device for exploring a mineral source in accordance with an exemplary embodiment. FIG. 2 is a sectional view of the portable UV device for exploring a mineral source, taken in a direction parallel to that of the top view of FIG. 1. Along section line A-A FIG. 3 is a bottom view of the portable UV device for exploring a mineral source shown in FIG. 1. FIG. 4 is a sectional view taken along line B-B' of FIG. 1. FIGS. 5A and 5B are perspective views illustrating a coupled relation between a body and a receiving container of an UV lamp assembly in accordance with an exemplary embodiment. FIGS. 6A and 6B are plan and sectional views illustrating a coupled relation between a body and a receiving container of an UV lamp assembly in accordance with another exemplary embodiment. FIG. 7 is a sectional view illustrating a coupled relation between a body and a receiving container of an UV lamp assembly in accordance with another exemplary embodiment.

Referring to FIGS. 1 to 4, a portable UV device 100 for exploring a mineral source in accordance with an exemplary embodiment includes a body 110, a visible component 120, an UV lamp assembly part 130, and a darkroom component 140. The portable UV device 100 for exploring a mineral source further includes power supply parts 150a and 150b, printed circuit boards 160a and 160b, switching parts 170a and 170b, and handle parts 180a and 180b.

The body 110 may have inner spaces 110a, 110b, and 110b'. The inner spaces 110a, 110b, and 110b' of the body 110 includes a first inner space 110a and a pair of second inner spaces 110b and 110b' spaced from each other with the first inner space 110a therebetween and extending in a first direction. The first inner space 110a may receive the power supply parts 150a and 150b and the printed circuit boards 160a and 160b and have a sealed structure. The second inner spaces 110b and 110b' may have downwardly opened structure and receive the UV lamp assembly parts 130a and 130b (note FIG. 3). To define the inner spaces 110a, 110b, and 110b', for example, the body 110 may include an upper plate 111, sidewalls 115 extending downward along an edge of the upper plate 111, partition walls 117 dividing a space defined by the upper plate 111 and the sidewalls 115 into three spaces. A lower plate 113 facing the upper plate 111 and covering a lower side of a middle space of the three spaces. The middle space of which the lower side is covered by the lower plate 113 may be the first inner space 110a, and spaces of which lower sides are not covered by the lower plate 113, that is, two spaces, each having an opened lower side, may be the second inner spaces 110b and 110b'. Although the body 110 has a rectangular shape in the drawings, if the body 110 has the above-described inner spaces, the body 110 is not specifically limited in shape. The body 110 may be formed of a material such as a plastic or metal. Also, if a material of the body 110 has a predetermined strength, the body 110 is not specifically limited in material.

The visible component 120 passes through the body 110 so that a mineral sample (not shown) disposed on a lower portion of the body 110 is viewed from an upper side of the body 110. In an exemplary embodiment, the visible component 120 may include a through tube 121 passing through the body 110 and having a tube shape, an upper transparent plate 123 coupled to the through tube 121 to cover upper and lower openings of the through tube 121, and a lower transparent plate 125. For example, the through tube 121 may pass through the first inner space 110a of the body 110, and each of the upper transparent plate 123 and the lower transparent plate 125 may be formed of transparent glass.

The UV lamp assembly 130 may emit UV rays onto the mineral sample disposed on the lower portion of the body 110. In an exemplary embodiment, the UV lamp assembly part 130 may include a first UV lamp assembly 130a and a second UV lamp assembly 130b which are spaced from each other with the visible component 120 there between.

The first UV lamp assembly 130a may be received into one of the second inner spaces 110b and 110b' of the body 110. The first UV lamp assembly 130a in accordance with an exemplary embodiment may include a first UV lamp 131a extending in a first direction, a first receiving container 133a coupled to the body 110 to receive the first UV lamp 131a, and a first UV filter 135a coupled to the first receiving container 133a to transmit only UV light having a specific wavelength of UV rays emitted from the first UV lamp 131a.

The first receiving container 133a (note FIG. 5B) may have a lamp receiving space in which the first UV lamp 131a is received. The lamp receiving space may extend in the first direction that is the extension direction of the first UV lamp 131a and have a structure opened toward a lower side of the body 110 so that the UV rays emitted from the first UV lamp 131a are emitted toward a lower portion of the body 110. The lamp receiving space of the first receiving container 133a may be defined by a reflective surface for reflecting the UV rays. The reflective surface of the lamp receiving space of the first receiving container 133a may reflect the UV rays emitted from the first UV lamp 131a. Thus, the UV rays emitted from the first UV lamp 131a may be guided in an opened direction of the lamp receiving space of the first receiving container 133a by the reflective surface and emitted to the outside. For example, at least one portion of the first receiving container 133a may be received into one of the second inner spaces 110b and 110b' of the body 110 and coupled to the body 110 so that the first receiving container 133a is rotated about a rotation axis parallel to the first direction that is the extension direction of the first UV lamp 131a.

In an exemplary embodiment, as shown in FIGS. 5A and 5B, at least one portion of the first receiving container 133a may be received into the downwardly opened second inner space 110b, and the first receiving container 133a may include coupling projections 137a and 137b protruding from the ends thereof with respect to the first direction. Also, coupling rings 119a and 119b having coupling grooves in which the coupling projections 137a and 137b of the first receiving container 133a are inserted respectively and are disposed on portions of the sidewalls 115 adjacent to both ends of the second inner space 110b with respect to the first direction. When the first receiving container 133a and the body 110 are coupled to each other by the coupling projections 137a and 137b of the first receiving container 133a and the coupling rings 119a and 119b disposed on the sidewalls 115 of the body 110, the first receiving container 133a may be rotated about the rotation axis parallel to the first direction. Thus, the UV rays emitted from the first UV lamp assembly 130a may be controlled in emission direction as illustrated in FIG. 4.

In another exemplary embodiment, as shown in FIGS. 6A and 6B, the first receiving container 133a may include coupling projections 137'a and 137'b respectively protruding from both ends with respect to a first direction. FIG. 6B is a sectional view taken along line B-B' or C-C' of FIG. 6A. Coupling holes in which the coupling projections 137'a and 137'b of the first receiving container 133a are respectively inserted to pass through sidewalls 115 defining both ends of the second inner space 110b with respect to the first direction and facing each other. When the coupling projections 137'a and 137'b of the first receiving container 133a are inserted into the coupling holes to pass through the sidewalls 115, thereby coupling the first receiving container 133a to the body 110, the first receiving container 133a may be rotated about the rotation axis parallel to the first direction. Thus, the UV rays emitted from the first UV lamp assembly 130a may be controlled in emission direction. To control rotation of the first receiving container 133a, the first receiving container 133a may also include a first rotation control part 139a protruding upward from a top surface thereof. In this case, the first rotation control part 139a may be inserted through the upper plate 111 of the body 110. Also, a first rotation slit 111a extending in a second direction crossing the first direction, for example, perpendicular to the first direction may be defined in the upper plate 111 of the body 110. When the first rotation control part 139a of the first receiving container 133a is reciprocated in the second direction in a state where the first rotation control part 139a is inserted into the first rotation slit 111a, the first receiving container 133a may be rotated about the rotation axis parallel to the first direction to adjust a moving distance of the first rotation control part 139a, thereby controlling the rotation amount of the first receiving container 133a.

In another exemplary embodiment, as shown in FIG. 7, the first receiving container 133a may include coupling projections 137''a and 137''b respectively protruding from both ends with respect to the first direction. Also, coupling holes in which the coupling projections 137''a and 137''b of the first receiving container 133a are respectively inserted to pass may be defined in the sidewalls 115 defining both ends of the second inner space 110b with respect to the first direction and facing each other. When the coupling projections 137''a and 137''b of the first receiving container 133a are inserted into the coupling holes to pass through the sidewalls 115, thereby coupling the first receiving container 133a to the body 110, the first receiving container 133a may be rotated about the rotation axis parallel to the first direction. Thus, UV rays emitted from the first UV lamp assembly 130a may be controlled in emission direction as illustrated in FIG. 4. To control the degree rotation of the first receiving container 133a, the first rotation control part 139'a may be coupled to one of the coupling projections 137''a and 137''b of the first receiving container 133a. When the first rotation control part 139'a is rotated about the rotation axis parallel to the first direction, the first receiving container 133a may be rotated also about the rotation axis parallel to the first direction to a rotation amount of the first rotation control part 139'a, thereby controlling the rotation amount of the first receiving container 133a.

The first UV filter 135a may be coupled to the first receiving container 133a to cover an opening of the lamp receiving space defined in the first receiving container 133a. The first UV filter 135a may transmit an UV ray having a specific wavelength of the UV rays emitted from the first UV lamp 131a.

The second UV lamp assembly 130b (note again FIG. 4) may be received into the other one of the second inner spaces 110b and 110b' of the body 110. The second UV lamp assembly 130b in accordance with an exemplary embodiment may include a second UV lamp 131b disposed parallel to the first UV lamp 131a, a second receiving container 133b coupled to the body 110 to receive the second UV lamp 131b, and a second UV filter 135b coupled to the second receiving container 133b to transmit only an UV ray having a specific wavelength of UV rays emitted from the second UV lamp 131b. The second receiving container 133b may have a lamp receiving space in which the second UV lamp 131b is received. The lamp receiving space may extend in a first direction that is the extension direction of the second UV lamp 131b and have a structure opened toward a lower side of the body 110 so that the UV rays emitted from the second UV lamp 131b is emitted toward the lower portion of the body 110. Also, the lamp receiving space of the second receiving container 133b may be defined by a reflective surface for reflecting the UV rays, like the lamp receiving space of the first receiving container 133a. At least one portion of the second receiving container 133b may be received into the other one of the second inner spaces 110b and 110b' of the body 110 and coupled to the body 110 so that the second receiving container 133b is rotated about a rotation axis parallel to the first direction that is the extension direction of the second UV lamp 131b.

In an exemplary embodiment, as shown in FIGS. 5A and 5B, at least one portion of the second receiving container 133b may be received into the downwardly opened second inner space 110b', and the second receiving container 133b may include coupling projections 137c and 137d respectively protruding from both ends thereof with respect to the first direction. Also, coupling rings 119c and 119d having coupling grooves in which the coupling projections 137c and 137d of the second receiving container 133b are inserted respectively and may be disposed on portions of the sidewalls 115 adjacent to both ends of the second inner space 110b' with respect to the first direction. As described above, when the second receiving container 133b and the body 110 are coupled to each other by the coupling projections 137c and 137d of the second receiving container 133b and the coupling rings 119c and 119d disposed on the sidewalls 115 of the body 110, the second receiving container 133b may be rotated about a rotation axis parallel to the first direction. Thus, the UV rays emitted from the second UV lamp assembly 130b may be controlled in emission direction.

In another exemplary embodiment, as shown in FIGS. 6A and 6B, the second receiving container 133b may include coupling projections 137'c and 137'd respectively protruding from both ends with respect to the first direction. Also, coupling holes in which the coupling projections 137"c and 137"d of the second receiving container 133b are respectively inserted to pass may be defined in the sidewalls 115 defining both ends of the second inner space 110b' with respect to the first direction and facing each other. When the coupling projections 137"c and 137"d of the second receiving container 133b are inserted into the coupling holes to pass through the sidewalls 115, thereby coupling the second receiving container 133b to the body 110, the second receiving container 133b may be rotated about the rotation axis parallel to the first direction. Thus, the UV rays emitted from the second UV lamp assembly 130b may be controlled in emission direction. To control a rotation amount of the second receiving container 133b, the second receiving container 133b may include a second rotation control part 139b protruding upward from a top surface thereof. In this case, the second rotation control part 139b may be inserted into the upper plate 111 of the body 110. Also, a second rotation slit 111b extending in a second direction crossing the first direction, for example, perpendicular to the first direction may be defined in the upper plate 111 of the body 110. When the second rotation control part 139b of the second receiving container 133b is reciprocated in the second direction in a state where the second rotation control part 139b is inserted into the second rotation slit 111b, the second receiving container 133b may be rotated about the rotation axis parallel to the first direction to adjust a moving distance of the second rotation control part 139b, thereby controlling the rotation amount of the second receiving container 133b.

In another exemplary embodiment, as shown in FIG. 7, the second receiving container 133b may include coupling projections 137"c and 137"d respectively protruding from both ends with respect to the first direction. Also, coupling holes in which the coupling projections 137"c and 137"d of the second receiving container 133b are respectively inserted to pass may be defined in the sidewalls 115 defining both ends of the second inner space 110b' with respect to the first direction and facing each other. When the coupling projections 137"c and 137"d of the second receiving container 133b are inserted into the coupling holes to pass through the sidewalls 115, thereby coupling the second receiving container 133b to the body 110, the second receiving container 133b may be rotated about the rotation axis parallel to the first direction. Thus, the UV rays emitted from the second UV lamp assembly 130b may be controlled in emission direction. To control a rotation amount of the second receiving container 133b, the second rotation control part 139'b may be coupled to one of the coupling projections 137"c and 137"d of the second receiving container 133b. When the second rotation control part 139'b is rotated about the rotation axis parallel to the first direction, the second receiving container 133b may be rotated also about the rotation axis parallel to the first direction to a rotation amount of the second rotation control part 139'b, thereby controlling the rotation amount of the second receiving container 133b.

The second UV filter 135b may be coupled to the second receiving container 133b to cover an opening of the lamp receiving space defined in the second receiving container 133b. The second UV filter 135b may transmit an UV ray having a specific wavelength of the UV rays emitted from the second UV lamp 131b.

The UV rays emitted from the first UV lamp assembly 130a and the UV rays emitted from the second UV lamp assembly 130b may overlap each other in an area spaced a predetermined distance from the lower plate 113 of the body 110. Also, since the first and second receiving containers 133a and 133b are rotatably coupled to the body 110 as described above, a distance between the lower plate 113 of the body 110 and the area in which the UV rays overlap each other may be adjusted as necessary.

Figure 8A:
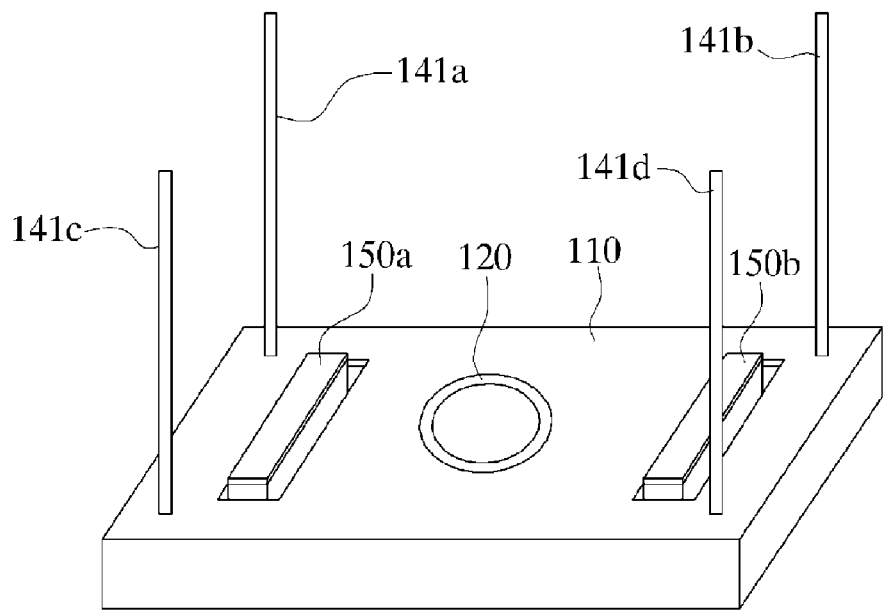
FIGS. 8A and 8B are perspective views illustrating a support for a darkroom component.
Figure 8B:
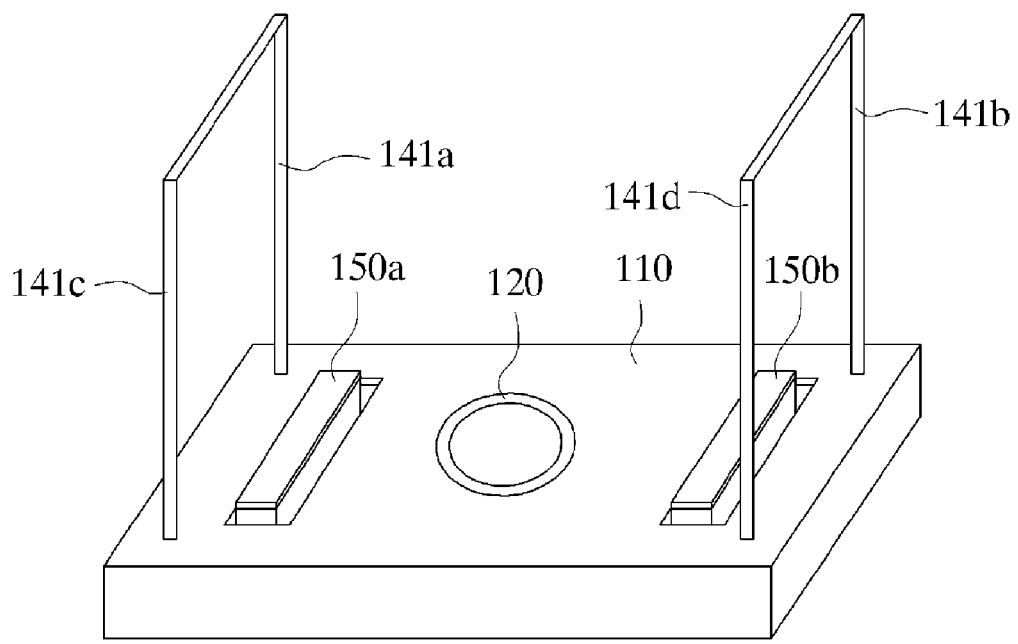
Figure 9:
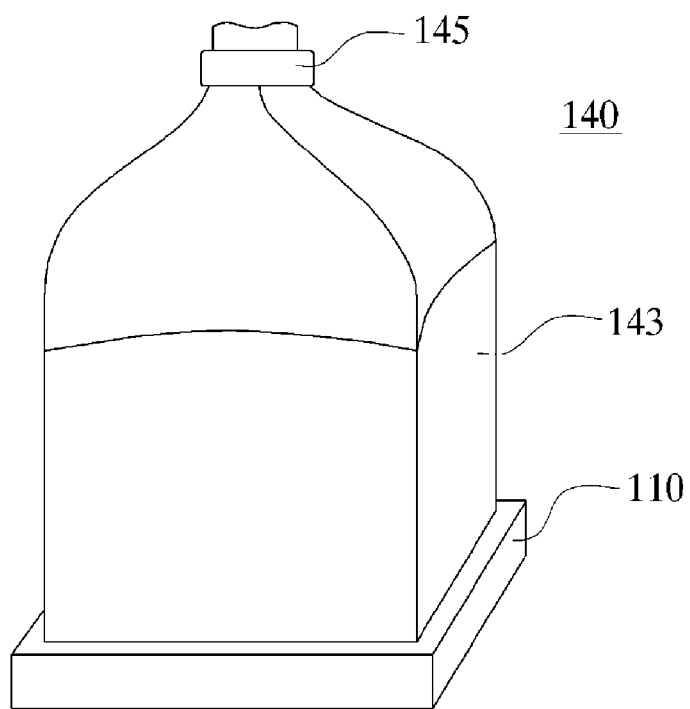
FIG. 9 is a perspective view of the darkroom component.

FIGS. 8A and 8B are perspective views illustrating support for a darkroom component. FIG. 9 is a perspective view of the darkroom component.

Referring to FIGS. 3, 4, 8A, and 9, the darkroom component 140 may be coupled to the lower plate 113 of the body 110 to surround the visible component 120 and the UV lamp assembly part 130 to define an external light blocking space in a lower portion of the lower plate 113. An inlet of the external light blocking space spaced from the lower plate 113 of the body 110 may be opened or closed.

For example, the darkroom component 140 may include a plurality of supports 141a, 141b, 141c, and 141d, a light blocking layer 143, and an opening/closing part 145.

The plurality of supports 141a, 141b, 141c, and 141d may be coupled to a bottom surface of the body 110. The plurality of supports 141a, 141b, 141c, and 141d may be coupled to the bottom surface of the body 110 so that a close curve defined by connecting points at which the plurality of supports 141a, 141b, 141c, and 141d are coupled to the body 110 to each other surrounds the visible component 120 and the first and second UV lamp assemblies 130a and 130b. For example, when the bottom surface of the body 110 has a rectangular shape having first and second sides and third and fourth sides connecting the first side to the second side, the plurality of supports 141a, 141b, 141c, and 141d may include a first support 141a disposed adjacent to a first vertex at which the first and third sides contact each other, a second support 141b disposed adjacent to a second vertex at which the first and fourth sides contacts each other, a third support 141c disposed adjacent to a third vertex at which the second and third sides contact each other, and a fourth support 141d disposed adjacent to a fourth vertex at which the second and fourth sides contact each other. The first to fourth supports 141a, 141b, 141c, and 141d may be rotatably coupled to bottom surfaces of the sidewalls 115. For example, each of the first to fourth supports 141a, 141b, 141c, and 141d may cross the bottom surface of the body 110 with respect to a point at which each support is coupled to the body 110, for example, by being rotated along a virtual vertical surface. As a result, an angle between the bottom surface of the body 110 and each of the supports 141a, 141b, 141c, and 141d may changed within a range from about 0° to about 100°.

When a mineral sample is observed using the portable UV device 100 for exploring a mineral resource, each of the supports 141a, 141b, 141c, and 141d may stand up at an angle of about 90° to about 100° with respect to the bottom surface of the body 110 to define a light blocking space. On the other hand, when the portable UV device is carried, each of the supports 141a, 141b, 141c, and 141d may be folded at an angle of about 0° with respect to the bottom surface of the body 110 to reduce the volume of the portable UV device 100 for exploring a mineral resource.

In an exemplary embodiment, as shown in FIG. 8A, the supports 141a, 141b, 141c, and 141d may be independently rotated with respect to each other, and ends of the supports 141a, 141b, 141c, and 141d may not be connected to each other. Alternatively, in another exemplary embodiment, as shown in FIG. 8B, ends adjacent to each other of the supports 141a, 141b, 141c, and 141d may be connected to each other.

The light blocking layer 143 may be coupled to the plurality of supports 141a, 141b, 141c, and 141d to define an external light blocking space. The external light blocking space defined by the light blocking layer 143 may have an inlet opened downward. The light blocking layer 143 may be formed of a material which may block external light and be easily curved or bent according to movement of the supports 141a, 141b, 141c, and 141d. For example, the light blocking layer 143 may be formed of a material such as an opaque vinyl, robber, or fabric.

The opening/closing part 145 may be coupled to the light blocking layer 143 to open or close the inlet of the external light blocking space. For example, the opening/closing part 145 may have a band-shaped structure coupled adjacent to a portion of the light blocking layer 143 in which the inlet of the external light blocking space is disposed. An easily detachable Velcro strip may be disposed on the ends of the band-shaped structure.

Referring again to FIGS. 1 to 4, the power supply parts 150a and 150b may be received in the first internal space 110a of the body 110 to supply required power to the UV lamp assemblies 130a and 130b. In an exemplary embodiment, when the UV lamp assemblies 130a and 130b include the first and second UV lamp assemblies 130a and 130b, the power supply parts 150a and 150b may include a first power supply part 150a for supplying power to the first UV lamp assembly 130a and a second power supply part 150b for supplying power to the second UV lamp assembly 130b. For example, each of the first and second power supply parts 150a and 150b may include a plurality of batteries. In another exemplary embodiment, although not shown, one power supply part may be provided to supply power to the first and second UV lamp assemblies 130a and 130b at the same time.

The printed circuit boards 160 and 160b transmit power supplied from the power supply parts 150a and 150b to the UV lamp assemblies 130a and 130b. In an exemplary embodiment, when the UV lamp assemblies 130a and 130b include the first and second UV lamp assemblies 130a and 130b and the power supply parts 150a and 150b include the first and second power supply parts 150a and 150b, the printed circuit boards 160a and 160b may include a first printed circuit board 160a electrically connected to the first power supply part 150a and the first UV lamp 131a to transmit the power supplied from the first power supply part 150a to the first UV lamp 131a and a second printed circuit board 160b electrically connected to the second power supply part 150b and the second UV lamp 131b to transmit the power supplied from the second power supply part 150b to the second UV lamp 131b. In another exemplary embodiment, although not shown, when one power supply part is provided to supply power the first and second UV lamp assemblies 130a and 130b at the same time, one printed circuit board electrically connected to the power supply part and the first and second UV lamps 131a and 131b to transmit the power supplied from the power supply part to the first and second UV lamps 131a and 131b may be provided.

The switching parts 170a and 170b may be electrically connected to the printed circuit boards 160a and 160b to control on/off operations of the UV lamp assemblies 130a and 130b, respectively. The switching parts 170a and 170b may be coupled to an outer surface of the upper plate 111 of the body 110. In an exemplary embodiment, when the UV lamp assemblies 130a and 130b include the first and second UV lamp assemblies 130a and 130b, the switching parts 170a and 170 may include a first switching part 170 for controlling an on/off operation of the first UV lamp assembly 130a and a second switching part 170b for controlling an on/off operation of the second UV lamp assembly 130b to independently operate the first and second UV lamp assemblies 130a and 130b. The first switching part 170a may be electrically connected to the first printed circuit board 160a, and the second switching part 170b may be electrically connected to the second printed circuit board 160b. The first switching part 170a may be disposed adjacent to a first handle part 180a that will be described later, and the second switching part 170b may be disposed adjacent to a second handle part 180b that will be described later.

Handle parts 180a and 180b may be coupled to outer surfaces of the sidewalls 115 of the body 110. In an exemplary embodiment, the handle parts 180a and 180b may include the first handle part 180a coupled to a first sidewall disposed adjacent to the first UV lamp assembly 130a of the sidewalls 115 of the body 110 and parallel to the first direction that is the extension direction of the first UV lamp 131a and the second handle part 180b coupled to a second sidewall facing the first sidewall of the sidewalls 115 of the body 110. Although each of the handle parts 180a and 180b are generally "C"-shaped structure in the drawings, the present disclosure is not limited thereto. For example, each of the handle parts 180a and 180b may have various shapes.

As described above, since the first and second UV lamp assemblies for emitting the UV rays so that the UV rays overlap each other on a position spaced a predetermined distance from the lower plate of the body are provided, fluorescent minerals may be explored using a low-output UV lamp. Also, since the first and second UV lamp assemblies are rotatable, the position in which the UV rays overlap each other may be changed. Also, since the darkroom component defines the external light blocking space in the lower portion of the body, the fluorescent minerals may be easily explored during the daytime. Also, since the supports are rotatably coupled to the body, the portable UV device for exploring a mineral resource may be easily portable.

Although exemplary embodiments have been described it will be readily understood by those skilled in the art that various modifications and changes can be made thereto without departing from the spirit and scope of the present disclosure defined by the appended claims.

What is claimed is:

1. A portable ultraviolet device for exploring a mineral resource, the portable ultraviolet device comprising:
    a body including a sealed first inner space and at least one second inner space opened downward;
    a visible component coupled to the body to pass through the sealed first inner space so that the mineral resource disposed at a lower portion of the body is observed from an upper side of the body;
    an ultraviolet lamp assembly emitting ultraviolet rays onto the mineral resource, the ultraviolet lamp assembly comprising an ultraviolet lamp extending in a first direction and a downwardly opened receiving container disposed in the second inner space coupled to the body to receive the ultraviolet lamp; and
    a darkroom component coupled to a bottom surface of the body to surround the visible component and the ultraviolet lamp assembly, the darkroom component defining an external light blocking space having an inlet in a lower portion of the body that is operable to selectively opened and closed;
    wherein the receiving container is rotatably coupled to the body about a first rotation axis parallel to the first direction.

2. The portable ultraviolet device of claim 1, wherein:
    the at least one second inner space comprises two second inner spaces mutually spaced from each other with the first inner space therebetween,
    the receiving container comprises a first receiving container rotatably coupled to the body about a first rotation axis parallel to the first direction and disposed in one of the two second inner spaces and a second receiving container rotatable coupled to the body about a second rotation axis parallel to the first direction and disposed in the other of the two second inner spaces,
    the ultraviolet lamp comprises a first ultraviolet lamp received in the first receiving container and a second ultraviolet lamp received in the second receiving container,
    the ultraviolet lamp assembly further comprises a first ultraviolet filter coupled to an opening of the first receiving container and a second ultraviolet filter coupled to an opening of the second receiving container.

3. The portable ultraviolet device of claim 2, further comprising:
    a first power supply received in the first inner space;
    a first printed circuit board received in the first inner space to transmit power from the first power supply to the first ultraviolet lamp;
    a second power supply received in the first inner space; and
    a second printed circuit board received in the first inner space to transmit power from the second power supply to the second ultraviolet lamp.

4. The portable ultraviolet device of claim 2, wherein:
    each of the first and second receiving containers comprises first and second coupling projections respectively protruding from both ends with respect to the first direction, and
    the bottom surface of the body comprises first and second coupling rings having coupling grooves in which the first and second coupling projections of the first receiving container are respectively inserted and third and fourth coupling rings having coupling grooves in which the first and second coupling projections of the second receiving container are respectively inserted.

5. The portable ultraviolet device of claim 2, wherein:
    each of the first and second receiving containers comprises third and fourth coupling projections respectively protruding from both end with respect to the first direction, and
    a sidewall of the body defining the second inner spaces has first and second coupling holes in which third and fourth coupling projections of the first receiving container are respectively inserted and third and fourth coupling holes in which third and fourth coupling projections of the second receiving container are respectively inserted.

6. The portable ultraviolet device of claim 5, further comprising:
    a first rotation member disposed outside the body, the first rotation member being coupled to one of the first and second coupling projections of the first receiving container to rotate the first receiving container about a rotation axis parallel to the first direction; and
    a second rotation member disposed outside the body, the second rotation member being coupled to one of the first and second coupling projections of the second receiving container to rotate the second receiving container about the rotation shaft parallel to the first direction.

7. The portable ultraviolet device of claim 5, wherein:
    first and second rotation slits extending in a second direction perpendicular to the first direction and spaced from each other are defined in a top surface of the body,
    the first receiving container comprises a first rotation member protruding upward, inserted into the first rotation slit, and rotated in the second direction to rotate the first receiving container about the rotation axis parallel to the first direction, and
    the second receiving container comprises a second rotation member protruding upward, inserted into the second rotation slit, and rotated in the second direction to rotate the second receiving container about the rotation axis parallel to the first direction.

8. The portable ultraviolet device of claim 1, wherein the darkroom component comprises:
    a plurality of supports arranged to surround the visible component and the ultraviolet lamp assembly, the plurality of supports being coupled to the bottom surface of the body to protrude from the bottom surface of the body;
    a light blocking layer coupled to the plurality of supports to define the external light blocking space; and
    an opening/closing part coupled to the light blocking layer to open or close an inlet of the external light blocking space.

9. The portable ultraviolet device of claim 8, wherein each of the plurality of supports is rotatably coupled to the bottom surface of the body.

10. A portable ultraviolet device for exploring a mineral resource, the portable ultraviolet device comprising:

a body having a sealed first central inner space and two lateral second inner spaces opened downward and mutually spaced from each other with the first inner space there between;

a visible component coupled to the body to pass through the body so that the mineral resource disposed at a lower portion of the body is observed from an upper side of the body;

an ultraviolet lamp assembly coupled to the body to emit ultraviolet rays onto the mineral resource, wherein the ultraviolet lamp assembly comprises:

a first ultraviolet lamp assembly inserted into one of the two second inner spaces and being coupled to the body and a second ultraviolet lamp assembly inserted into the other of the two second inner spaces and being coupled to the body, wherein the first ultraviolet lamp assembly comprises a first ultraviolet lamp extending in a first direction, a downwardly opened first receiving container rotatably coupled to the body about a first rotation axis parallel to the first direction to receive the first ultraviolet lamp, and a first ultraviolet filter coupled to an opening of the first receiving container, and the second ultraviolet lamp assembly comprises a second ultraviolet lamp extending in the first direction, a downwardly opened second receiving container rotatably coupled to the body about a second rotation axis parallel to the first direction to receive the second ultraviolet lamp, and a second ultraviolet filter coupled to an opening of the second receiving container;

a first power supply received in the first inner space;

a first printed circuit board received in the first inner space to transmit power from the first power supply to the first ultraviolet lamp;

a second power supply received in the first inner space;

a second printed circuit board received in the first inner space to transmit power from the second power supply to the second ultraviolet lamp; and a darkroom component coupled to a bottom surface of the body to surround the visible component and the ultraviolet lamp assembly, the darkroom component defining an external light blocking space having a selectively openable inlet in a lower portion of the body.

11. The portable ultraviolet device of claim 10, wherein:
each of the first and second receiving containers comprises first and second coupling projections respectively protruding from both ends with respect to the first direction, and the bottom surface of the body comprises first and second coupling rings having coupling grooves in which the first and second coupling projections of the first receiving container are respectively inserted and third and fourth coupling rings having coupling grooves in which the first and second coupling projections of the second receiving container are respectively inserted.

12. The portable ultraviolet device of claim 11, wherein:
first and second rotation slits extending in a second direction perpendicular to the first direction and spaced from each other are defined in a top surface of the body;

the first receiving container comprises a first rotation member protruding upward, inserted into the first rotation slit, and rotated in the second direction to rotate the first receiving container about the rotation axis parallel to the first direction; and the second receiving container comprises a second rotation member protruding upward, inserted into the second rotation slit, and rotated in the second direction to rotate the second receiving container about the rotation axis parallel to the first direction.

* * * * *